(12) United States Patent
Michienzi et al.

(10) Patent No.: US 9,983,178 B2
(45) Date of Patent: May 29, 2018

(54) CHROMATOGRAPHY COLUMN ASSEMBLY

(75) Inventors: Joseph D. Michienzi, Millbrook, MA (US); Keith Fadgen, Hope Valley, RI (US); Wade P. Leveille, Sr., Douglas, MA (US); Raymond P. Fisk, Norton, MA (US); Frank John Marzalkowski, Jr., Cumberland, RI (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 327 days.

(21) Appl. No.: 14/238,278

(22) PCT Filed: Aug. 23, 2012

(86) PCT No.: PCT/US2012/051972
§ 371 (c)(1),
(2), (4) Date: Feb. 11, 2014

(87) PCT Pub. No.: WO2013/032832
PCT Pub. Date: Mar. 7, 2013

(65) Prior Publication Data
US 2014/0166562 A1 Jun. 19, 2014

Related U.S. Application Data

(60) Provisional application No. 61/527,638, filed on Aug. 26, 2011, provisional application No. 61/527,639, (Continued)

(51) Int. Cl.
*G01N 30/60* (2006.01)
*B01D 15/10* (2006.01)
(Continued)

(52) U.S. Cl.
CPC ......... *G01N 30/6026* (2013.01); *B01D 15/10* (2013.01); *B01D 15/22* (2013.01);
(Continued)

(58) Field of Classification Search
CPC .... B01D 15/14; B01D 15/1871; B01D 15/22; B01D 15/10; B01D 15/16; F16L 9/14;
(Continued)

(56) References Cited

U.S. PATENT DOCUMENTS

| 4,116,836 A | 9/1978 | DeAngelis |
| 5,044,190 A | 9/1991 | Hoff et al. |

(Continued)

FOREIGN PATENT DOCUMENTS

| EP | 1399641 A1 | 3/2004 |
| GB | 2084063 | 4/1982 |

(Continued)

OTHER PUBLICATIONS

Extended European Search Report in counterpart European Patent Application No. 12828910.5, dated Mar. 19, 2015; 7 pages.
(Continued)

*Primary Examiner* — Katherine Zalasky
*Assistant Examiner* — Benjamin L Lebron
(74) *Attorney, Agent, or Firm* — Schmeiser, Olsen & Watts LLP

(57) ABSTRACT

Described is a chromatography column assembly that includes a permanently deformable outer tube, an intermediate tube, an inner tube and a sorbent bed disposed within the inner tube. The sorbent bed may be in the form of packed chromatographic particles or a porous monolithic structure. A radial seal is provided by one or more uniform radial crimps at longitudinal locations on the assembly. The uniform radial crimp compresses the outer tube and underlying intermediate tube onto the inner tube to achieve a high pressure liquid tight seal between the three tubes. The length and depth of each crimp is accurately formed to accommodate the requirements of the particular application. Leakage along the tubing assembly is prevented and void volume is
(Continued)

reduced or eliminated. No external ferrule or ferrule swaging mechanism is needed; therefore the chromatography column assembly is easily adapted for use in various chromatographic column configurations.

20 Claims, 7 Drawing Sheets

Related U.S. Application Data filed on Aug. 26, 2011, provisional application No. 61/527,747, filed on Aug. 26, 2011, provisional application No. 61/527,648, filed on Aug. 26, 2011, provisional application No. 61/621,852, filed on Apr. 9, 2012.

(51) Int. Cl.
*B01D 15/22* (2006.01)
*B05B 5/16* (2006.01)
*G01N 30/72* (2006.01)
*B01D 15/18* (2006.01)

(52) U.S. Cl.
CPC ............ *B05B 5/16* (2013.01); *G01N 30/60* (2013.01); *G01N 30/603* (2013.01); *G01N 30/6052* (2013.01); *B01D 15/1871* (2013.01); *G01N 30/6004* (2013.01); *G01N 30/6039* (2013.01); *G01N 30/6095* (2013.01); *G01N 30/7266* (2013.01); *Y10T 29/49908* (2015.01)

(58) Field of Classification Search
CPC ........... F16L 19/02; F16L 13/141; F17D 1/00; B29C 65/562; B29C 66/1142; B29L 2031/756; G01N 30/6026; G01N 30/603; G01N 30/60; G01N 30/6052; G01N 30/7266; G01N 30/6095; G01N 30/6039; G01N 30/6004; Y10T 29/49908
See application file for complete search history.

(56) References Cited

U.S. PATENT DOCUMENTS

| | | | |
|---|---|---|---|
| 5,316,262 A | | 5/1994 | Bruce et al. |
| 5,651,885 A | | 7/1997 | Shick |
| 5,800,692 A | | 9/1998 | Naylor et al. |
| 6,039,084 A | | 3/2000 | Martucci et al. |
| 6,139,732 A | * | 10/2000 | Pelletier ................ B01D 15/14 210/198.2 |
| 2003/0183566 A1 | | 10/2003 | Laub et al. |
| 2004/0035774 A1 | | 2/2004 | Horsman et al. |
| 2005/0092182 A1 | | 5/2005 | Gerner et al. |
| 2006/0016499 A1 | | 1/2006 | Blanchard et al. |
| 2007/0068872 A1 | | 3/2007 | Gerhardt et al. |
| 2007/0138076 A1 | | 6/2007 | Daridon et al. |
| 2009/0257835 A1 | | 10/2009 | Lysobey et al. |
| 2013/0126021 A1 | * | 5/2013 | Hobbs ................ G01N 30/6039 137/557 |

FOREIGN PATENT DOCUMENTS

| | | |
|---|---|---|
| GB | 2431971 | 5/2007 |
| WO | 9906748 | 2/1999 |
| WO | 2005087340 | 9/2005 |
| WO | 2006091952 | 8/2006 |
| WO | 2009088663 A1 | 7/2009 |
| WO | 2013072755 | 5/2013 |
| WO | 2013113386 | 8/2013 |

OTHER PUBLICATIONS

International Preliminary Report on Patentability in counterpart international patent application No. PCT/US12/51972, dated Mar. 13, 2014; 6 pages.
International Search Report & Written Opinion in related international patent application No. PCT/US12/51972, dated Jan. 23, 2013; 7 pages.
International Search Report and Written Opinion in related international patent application No. PCT/US12/51974, dated Nov. 16, 2012; 8 pages.
International Preliminary Report on Patentability in related international patent application No. PCT/US12/51974, dated Mar. 13, 2014; 7 pages.
Extended European Search Report in related European Patent Application No. 12826799.4, dated Feb. 27, 2015; 10 pages.
Kortmann, et al., "A rapid, reliable, and automatable lab-on-a-chip interface", Lab on A Chip, Mar. 3, 2009, pp. 1455-1460, vol. 9, The Royal Society of Chemistry.
Restriction Requirement in related U.S. Appl. No. 14/233,212, dated Jan. 8, 2016; 8 pages.
Non-Final Office Action in related U.S. Appl. No. 14/233,212, dated May 12, 2016; 10 pages.
Final Office Action in related U.S. Appl. No. 14/233,212, dated Sep. 2, 2016; 8 pages.
Final Office Action in related U.S. Appl. No. 14/233,212, dated Feb. 21, 2017; 10 pages.
Examination Report in European Patent Application No. 12826799.4 dated Apr. 11, 2017; 9 pages.

* cited by examiner

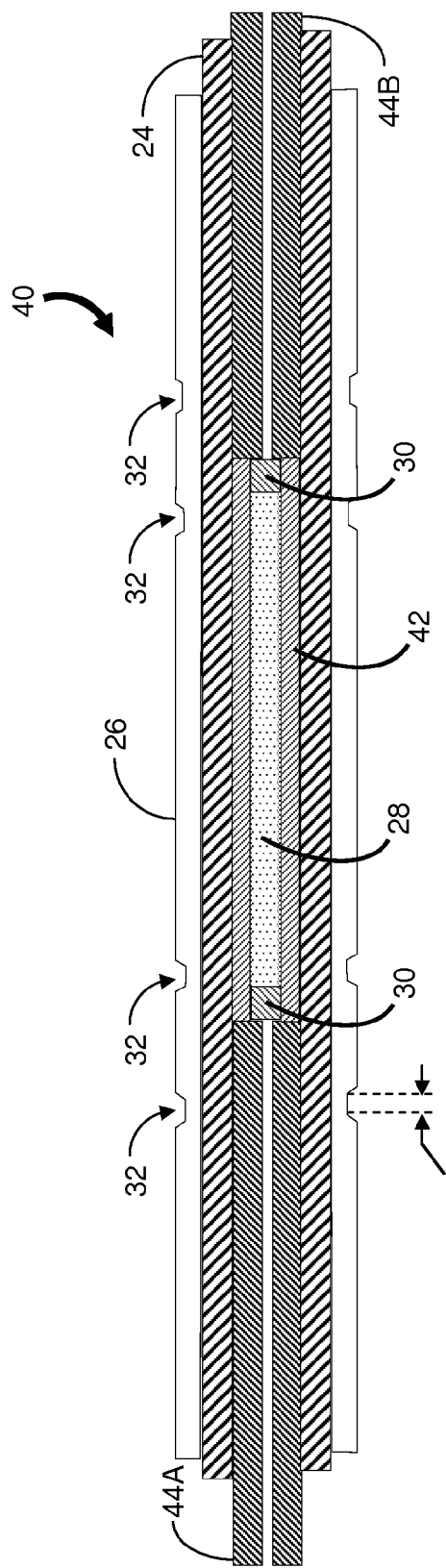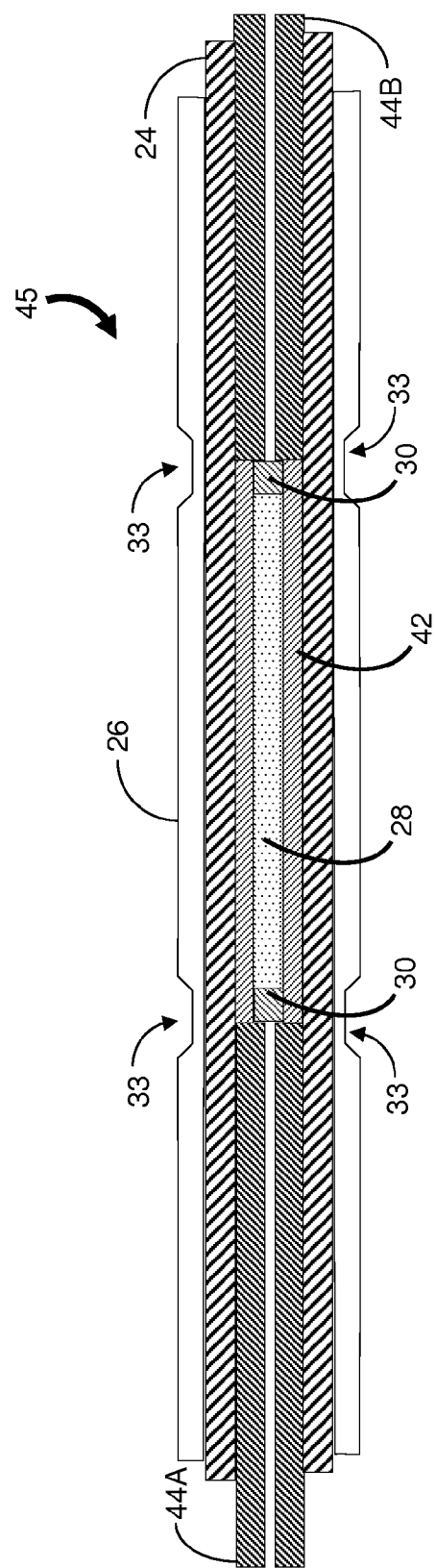

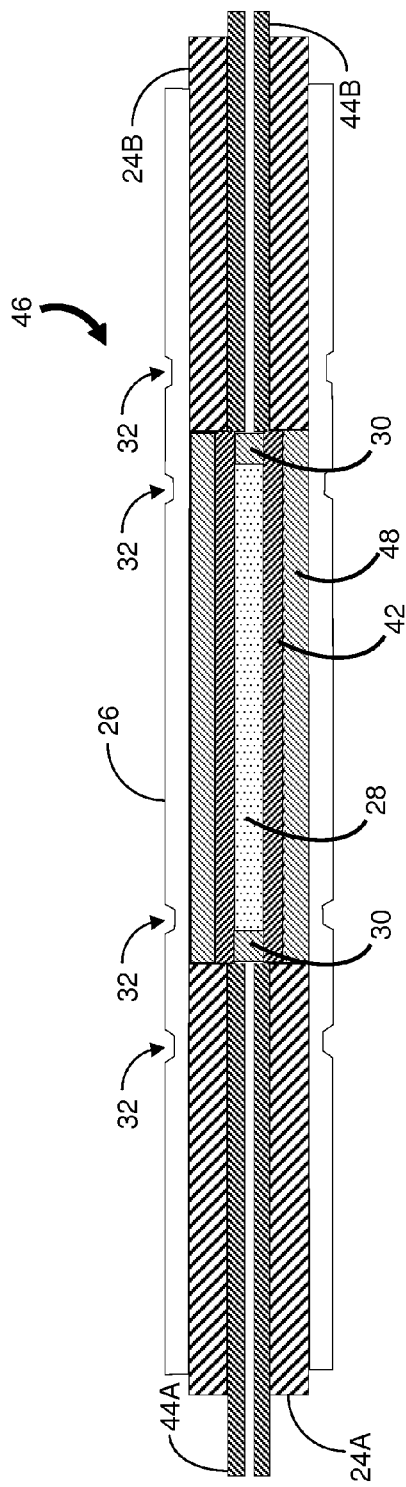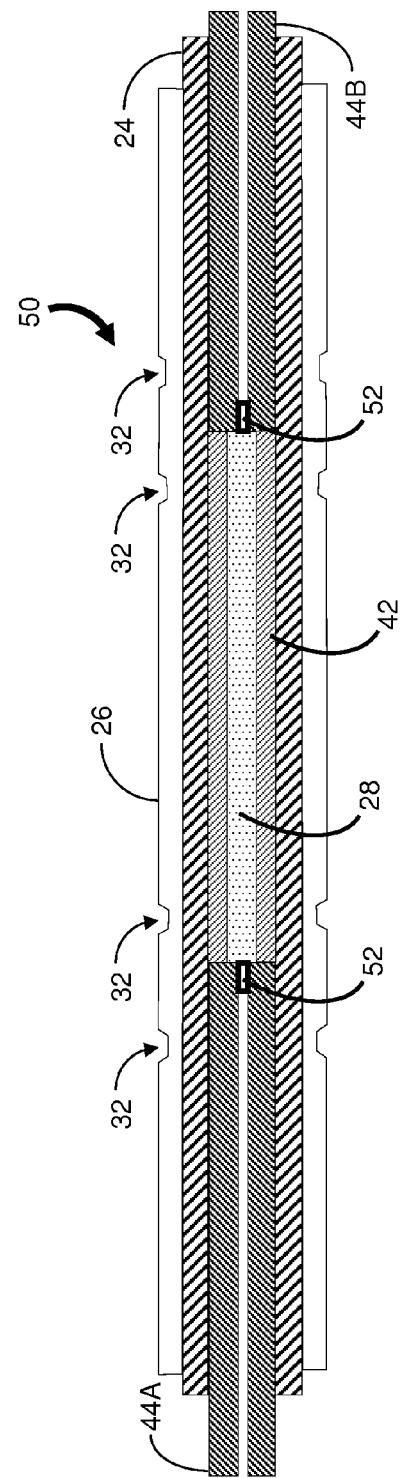

CHROMATOGRAPHY COLUMN ASSEMBLY

RELATED APPLICATIONS

This application claims the benefit of the earlier filing date of U.S. Provisional Patent Application Ser. No. 61/527,638, filed Aug. 26, 2011 and titled "Reusable Fitting for Attaching a Conduit to a Port," U.S. Provisional Patent Application Ser. No. 61/527,639, filed Aug. 26, 2011 and titled "Chromatography Apparatus with Diffusion-Bonded Coupler," U.S. Provisional Patent Application Ser. No. 61/527,747, filed Aug. 26, 2011 and titled "Liquid-Chromatography Conduit Assemblies Having High-Pressure Seals," U.S. Provisional Patent Application Ser. No. 61/527,648, filed Aug. 26, 2011 and titled "Electrospray Assembly for a Microfluidic Chromatography Apparatus," and U.S. Provisional Patent Application Ser. No. 61/621,852, filed Apr. 9, 2012 and titled "Chromatography Column Assembly," the entireties of which are incorporated herein by reference.

FIELD OF THE INVENTION

The invention relates generally to chromatography apparatus that operate at high pressures. More particularly, the invention relates to conduit assemblies that include conduits terminated or joined in a manner that provides high pressure seals such as chromatographic column assemblies.

BACKGROUND

Various types or forms of conduits, such as tubes, columns and linear flow cells are used in analytical instrumentation for transporting and/or processing fluids and samples. For example, chemical analysis instruments that utilize liquid chromatography (LC), high performance liquid chromatography (HPLC), capillary electrophoresis (CE) or capillary electro-chromatography (CEC) perform separation of a sample as the mobile phase containing the sample passes through a separation column, or concentrate a sample in a trap column before delivery of the concentrated sample to a separation column. For example, when a LC system is coupled to a light detector, linear tubes or flow cells are used to contain a fluid for optical analysis. Moreover, when a capillary LC system is interfaced to a mass spectrometer (MS), such as an electrospray ionization mass spectrometer (ESI-MS) instrument, a liquid sample processed by LC is typically pumped through a conduit to an electrospray tip. A high voltage is applied to the tip so that the liquid sample is transformed into charged particles for mass spectroscopic analysis.

Tubing used in analytical apparatus is required to withstand pressures encountered during fabrication and operation. Moreover, the tubing should be reliable for repeated use and have physical and chemical compatibility with process and sample compounds. Generally, tubing material should not corrode or leach, and sample compounds should not adhere to the tubing unless such compounds are required for a separation process.

For high pressure applications, such as HPLC applications, the tubing is typically made from stainless steel or fused silica to provide suitable strength and cleanliness. Fused-silica tubes are commonly used in capillary chromatographic systems due to desirable features. For example, the dimensions of fused silica tubing can be easily controlled during manufacturing. In addition, the wall of fused-silica tubing is clean, non-reactive and smooth, thus providing good transport of small volumes of fluids. A significant disadvantage of fused silica tubing is its vulnerability to fracturing and breaking.

Typically, tubing must be compatible with connectors which provide fluidic connections to various apparatus components. Problems associated with the use of connectors are particularly prominent for high-pressure fabrication and operation, for example, pressures in a range of 10,000 to 18,000 pounds per square inch (psi), as connectors can be the source of fluid leaks. Tubing connections should also minimize void volume, especially for systems having reduced tubing and component dimensions.

SUMMARY

In one aspect, the invention features a chromatographic column assembly which includes an outer tube comprising a metal, an intermediate tube comprising a polymeric material and disposed within the outer tube, an inner tube disposed within the intermediate tube, and a sorbent bed disposed within the inner tube. The outer tube is deformed by a uniform radial crimp at a longitudinal location along the outer tube to form a fluid-tight seal between the outer tube, intermediate tube and inner tube. The uniform radial crimp has a base region in which a diameter of the outer tube is reduced for a non-zero longitudinal length.

In another aspect, the invention features a chromatographic column assembly which includes an outer tube comprising a metal, an intermediate tube comprising a polymeric material and disposed within the outer tube, and an inner tube formed of fused silica and disposed within the intermediate tube. The chromatographic column assembly also includes a sorbent bed disposed within the inner tube and a pair of frits. Each frit is disposed at an end of the sorbent bed. The outer tube, intermediate tube, sorbent bed tube and one of the frits each have a first end that is polished flush with the other first ends and the outer tube, intermediate tube, sorbent bed and the other frit each has a second end that is polished flush with each of the other second ends. The outer tube is deformed at a first uniform radial crimp at a longitudinal location proximate to the first ends to thereby form a fluid-tight seal between the outer tube, intermediate tube, sorbent bed tube and one of the frits. The outer tube is deformed at a second uniform radial crimp at a longitudinal location proximate to the second ends to thereby form a fluid-tight seal between the outer tube, intermediate tube, sorbent bed tube and the other of the frits, the first and second uniform radial crimps having a base region in which a diameter of the outer tube is reduced for a non-zero longitudinal length.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 2 is a cross-sectional diagram of an embodiment of a chromatography column in accordance with the invention.

FIG. 3 is a cross-sectional diagram of another embodiment of a chromatography column in accordance with the invention.

FIG. 4 is a cross-sectional diagram of another embodiment of a chromatography column assembly in accordance with the invention.

FIG. 5 is a cross-sectional diagram of another embodiment according to the invention in which a chromatography column assembly has a frit immobilized inside each end of a fluid transfer tube.

DETAILED DESCRIPTION

Figure 1A:
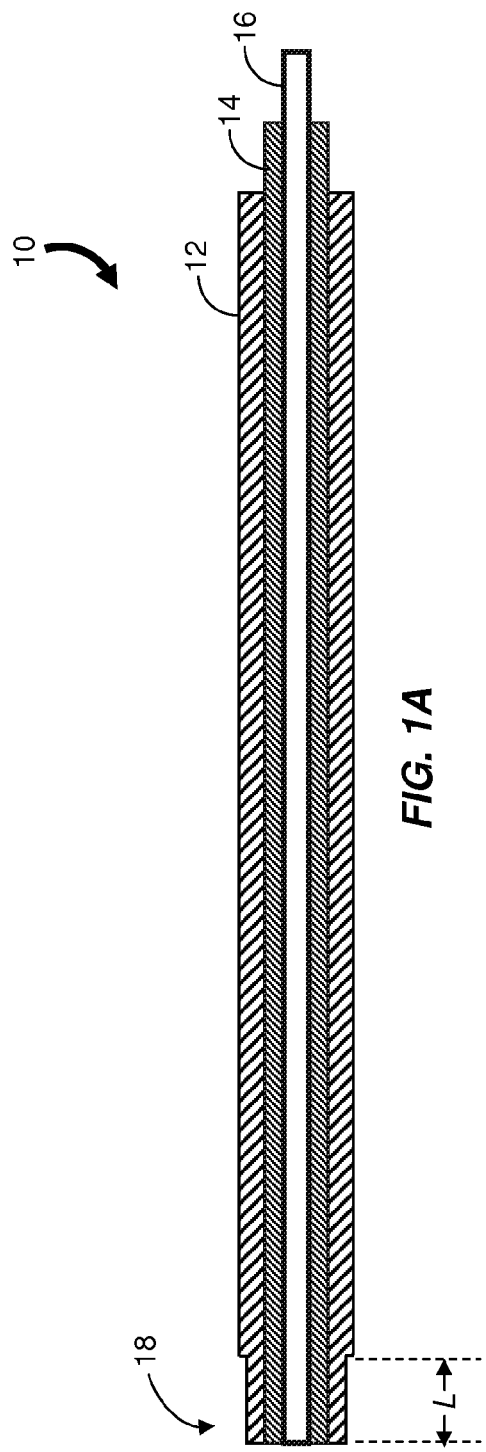
FIG. 1A is a cross-sectional diagram of an embodiment of a tubing assembly in accordance with the invention.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The term "capillary", as used herein, refers to tubes having an inner diameter of no greater than about 500 µm. Depending on context, the words "capillary" and "conduit" are used interchangeably herein.

The term "connector", as used herein, refers to any object or mechanism, or part of an object or mechanism, which joins pieces together or connects one mechanical part to another, such as fittings, unions, tees and couplers.

As used herein, the words "crimping" refers to the joining of two or more malleable materials, such as metals, by deforming one or both materials to secure the materials to each other. The word "crimp" refers to the deformity or bend in one or more of the materials caused by the crimping process.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

In brief overview, the invention relates to a chromatography column assembly, such as a chromatography separation column assembly or a chromatography trap column assembly. The chromatography column assembly includes a three component tubing assembly that includes a permanently deformable outer tube, an intermediate tube and an inner tube. A radial seal is provided, for example, through one or more uniform radial crimps at one or more longitudinal locations on the tubing assembly. At least one uniform radial crimp is applied at one or more longitudinal locations along the outer tube to permanently deform and compress the outer tube and underlying intermediate tube onto the inner tube to achieve a high pressure liquid tight seal between the three tubes. The length and depth of each crimp can be formed to accommodate the requirements of the particular application. The term "uniform radial crimps", as used in this application, refers to crimps formed by a compression force that is applied equally in all radial directions, 360 degrees, around a tube or a tubing assembly. Thus leakage along the tubing assembly is prevented and void volume is reduced or eliminated.

Advantageously, the uniform radial crimps are not formed using conventional ferrules which result in single narrow line crimps having minimal longitudinal length and crimp depths that are difficult to control. The uniform radial crimps present in the various embodiments of chromatography column assemblies disclosed herein are accurately shaped and include a base region where the diameter of the outer tube is reduced in a controlled manner over an extended (i.e., non-zero) longitudinal length. By way of examples, the longitudinal length may be less than 1.0 mm or greater than 6 mm.

The inner tube includes a sorbent bed which may be comprised of a packed bed of chromatographic particles. As an alternative to a packed bed, the sorbent may also be in the form of a porous monolithic structure. One or more frits may be adhered to the sorbent bed at one or both ends to retain the particles within the sorbent bed. Frits may be formed of a thermoset polymer, such as a siloxane-based thermoset polymer, and held in place by sintering the thermoset polymer or by other suitable chemical or physical immobilization techniques.

No external ferrule or ferrule swaging mechanism is needed therefore the chromatography column assemblies are easily adapted for use in various chromatographic column designs. The invention is particularly useful for making high pressure, low dispersion fluidic connections between fluid transfer lines and a crimped tube assembly containing a packed sorbent bed. The design approach can easily accommodate differences in the inside or outside dimensions of the tubes being joined. This is particularly useful in nano and micro scale column designs, where volumes should be minimized, and it is desirable for the inside diameter of fluid transfer lines to be smaller than the internal diameter of the sorbent bed. The column assembly can include materials in the flow path that are well suited for micro and nano scale separations. Such materials include the PEEK family of polymers for the intermediate tube and fused silica capillary for the inner tube. Hard, permanently deformable materials, such as stainless steel, are preferred for the outer tube. Chromatographic column assemblies constructed according to principles of the invention are capable of withstanding pressures in excess of 20,000 psi and are suitable for sorbent beds having particles smaller than 2 µm.

Figure 1C:
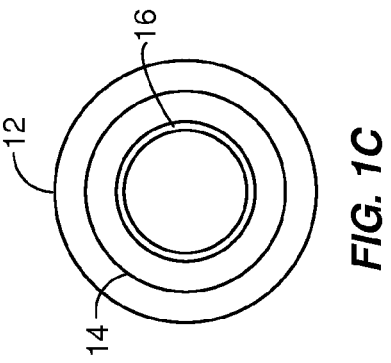
FIG. 1C is a view of the proximal end of the tubing assembly of FIG. 1A.
Figure 1B:
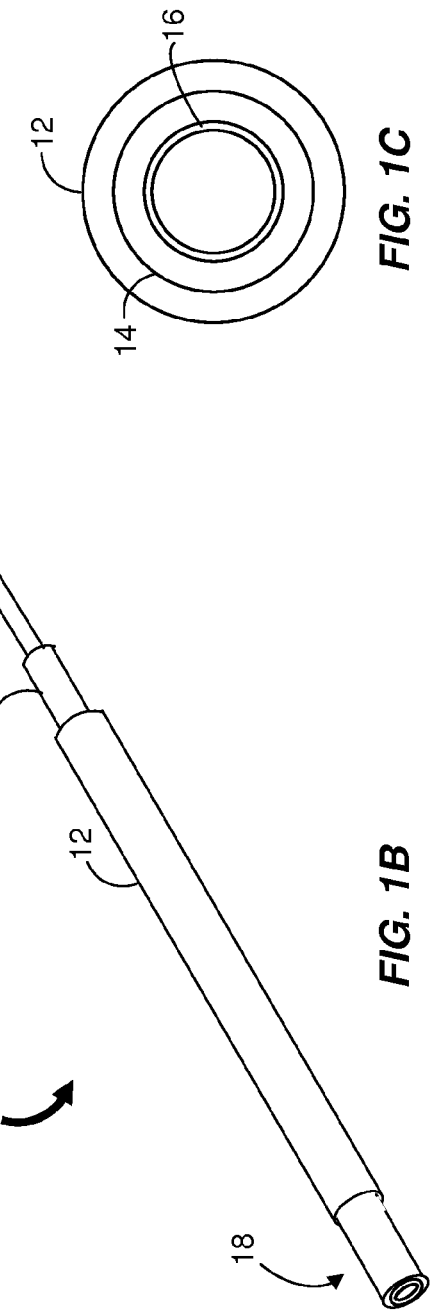
FIG. 1B is a three-dimensional view of the tubing assembly of FIG. 1A.

FIG. 1A and FIG. 1B are a cross-sectional diagram and a three-dimensional view of a tubing assembly 10 in accordance with one embodiment of the invention. The assembly 10 includes an outer tube 12, an intermediate tube 14 disposed within the outer tube 12 and an inner tube 16 disposed within which the intermediate tube 14. A radial seal between the tubes 12,14,16 is formed by deforming the outer tube 12 to press the intermediate tube 14 against the inner tube 16 to achieve a uniform radial crimp 18 at an end of the tubing assembly 10. The longitudinal length L and depth of the uniform radial crimp 18 can be selected according to the requirements of a particular application. The radial seal formed by this process can withstand pressures that can exceed 18,000 psi. In some embodiments, two or more uniform radial crimps are formed at different longitudinal locations along the tubing assembly 10 with one of the crimps formed at an end of the tubing assembly 10.

In some embodiments of a method of making a tubing assembly, the uniform radial crimp 18 is produced by a pneumatic or hydraulic collet having a circular bore. The collet is machined to produce the desired length, diameter and shape of the crimp, then positioned to encircle an end of the tubing assembly 10 and is compressed uniformly around the tubing assembly 10.

The proximal end (having the crimp 18) of the tubing assembly 10 is polished such that the outer, intermediate and inner tubes 12, 14, 16 all terminate in a plane that is perpendicular to a longitudinal axis of the tubing assembly 10 as shown in FIG. 1C. In some implementations, more than one crimp is formed at the polished end to consolidate a fluid-tight seal along the tubing assembly 10.

In alternative embodiments, one or both ends of the tubing assembly are trimmed or shaped to be compatible with other fluidic components, such as connectors, which, for example, mate with large diameter metallic tubing to obtain substantially fluid-tight and durable plumbing connections at pressures up to 18,000 psi or greater.

The inner tube may be implemented as a chromatography column, such as an analytical column or a trap column. In such embodiments, one or more frits are optionally provided at one or both ends of the inner tube to help retain a packing material in the column without substantial increase of void volume. The fritted end of the tube is optionally heated to sinter the packing material. Upon completion of the frit, the remaining unpacked space of the tube may be filled with packing material. For example, a frit can be formed from a siloxane-based thermoset polymer such as poly dimethyl siloxane ("PDMS").

The outer, intermediate, and inner tubes 12, 14, 16 are each fabricated in any desired dimensions in any suitable manner from any suitable materials. For example, the inner tube 16 can be formed of stainless steel or, more commonly, fused silica. The intermediate tube 14 can be formed of a polymeric material, for example, VICTREX® PEEK polymer available from Victrex PLC, Lancashire, United Kingdom or PEEKsil™ polymer available from SGE Analytical Science, Pty Ltd, Victoria, Australia. The outer tube 12 is formed of a metallic material, for example, hardened or annealed steel. A hardened steel reduces the occurrences of accidental bending.

In one particular example, a completed tubing assembly includes an inner tube 16 having an inner diameter (ID) of about 30 μm and an outer diameter (OD) of about 360 μm. The intermediate tube 14 has an ID of about 380 μm, which is slightly greater than the OD of the inner tube 16, and an OD of about 760 μm. The outer tube 12 has an OD slightly greater than about 1000 μm. The ID of the outer tube 12 is selected to be compatible with the OD of the intermediate tube 14, that is, to be slightly greater than about 760 μm. Thus the inner tube 16 can be inserted into the intermediate tube 14 and the intermediate tube 14 can be inserted into the outer tube 12. Preferably, during insertion, there is some contact between the circumference of the intermediate tube 14 and the inner circumference of the outer tube 12. It should be appreciated that this example is merely illustrative and non-limiting.

FIG. 2 shows an embodiment of a chromatography column assembly 40. Similar to the inner tube 16 in the tubing assembly 10 of FIG. 1, two inner tubes 44A and 44B (i.e., fluid transfer tubes) are disposed within an intermediate tube 24. In addition, a sorbent bed tube 42 is disposed within the intermediate tube 24 between the two inner tubes 44. Each fluid transfer tube 44 has an end that is proximate to or abutting an end of the sorbent bed tube 42. A sorbent bed 28 is disposed within the sorbent bed tube 42 and a frit 30 is chemically or physically immobilized inside the sorbent bed tube 42 at each end.

A uniform radial crimp 32 is formed on the outer tube 26 at a longitudinal location on each side of each frit 30. Each crimp 32 includes a base region having a longitudinal length L where the diameter of the outer tube 26 is at a constant lesser value. Each crimp 32 also includes a transition region on each side of the crimp base where the tube diameter transitions between the smaller diameter and the outer tube diameter 26. One advantage of the illustrated uniform radial crimp 32 relative to a radial crimp that is formed by a standard ferrule is that the crimp base region can be formed to a desired length to achieve the desired properties for a particular application. In addition, the diameter and shape of the uniform radial crimps 32 are more accurately controlled.

The uniform radial crimps 32 can be formed by applying a compression force equally in all radial directions around the column assembly 20. In some embodiments, the crimps 32 are produced by a collet having a machined circular bore. The collet is positioned to encircle an end of the column assembly 20 and then radially compressed. By way of a specific example, a 5C machine collet, available from Hardinge Workholding Group of Elmira, N.Y., USA, can be machined to produce a controlled length and diameter circular crimp upon activation using a standard collet chuck. The collet chuck can be activated using a hydraulic or pneumatic force, or any other suitable force that achieves the desired radial compression.

In some embodiments, the inner tubes 44 intermediate tube 24 and outer tube 26 are formed from fused silica, a polymeric material (e.g., PEEK) and stainless steel, respectively.

In various embodiments, the sorbent bed 28 is formed of a chromatographic sorbent such as porous silica particles that are surface derivatized with specific functional groups. In other embodiments, polymeric and inorganic-organic hybrid based particles can be used. The sorbent bed 28 may comprise a packed bed of particles, or alternatively, may be a monolithic structure.

In alternatives to the embodiment illustrated in FIG. 2, each pair of uniform radial crimps 32 is replaced by a single uniform radial crimp having an increased longitudinal length that spans the longitudinal section to be sealed. For example, FIG. 3 shows an embodiment of a chromatography column assembly 45 in which a single uniform radial crimp 33 is used to seal at a longitudinal location wherein the sorbent bed tube 42 and a respective frit 30 abut each of the inner tubes 44.

FIG. 4 shows an alternative embodiment of a chromatography column assembly 46 in which the diameters of the sorbent bed 28 and sorbent bed tube 42 are larger than for the assembly 40 of FIG. 3. To maintain the same dimensions of the outer tube 26, a separate intermediate tube 48 is used along the length of the sorbent bed tube 42. The separate intermediate tube 48 has a reduced wall thickness so that its outer diameter (OD) is the same as the OD of the other intermediate tubes 24.

FIG. 5 shows an alternative embodiment of a chromatography column assembly 50 in which a frit 52 is chemically or physically immobilized inside and at the end of each fluid transfer tube 44. In this embodiment, the sorbent bed 28 is not subject to overheating when the frits 52 are sintered at elevated temperatures.

Figure 6:
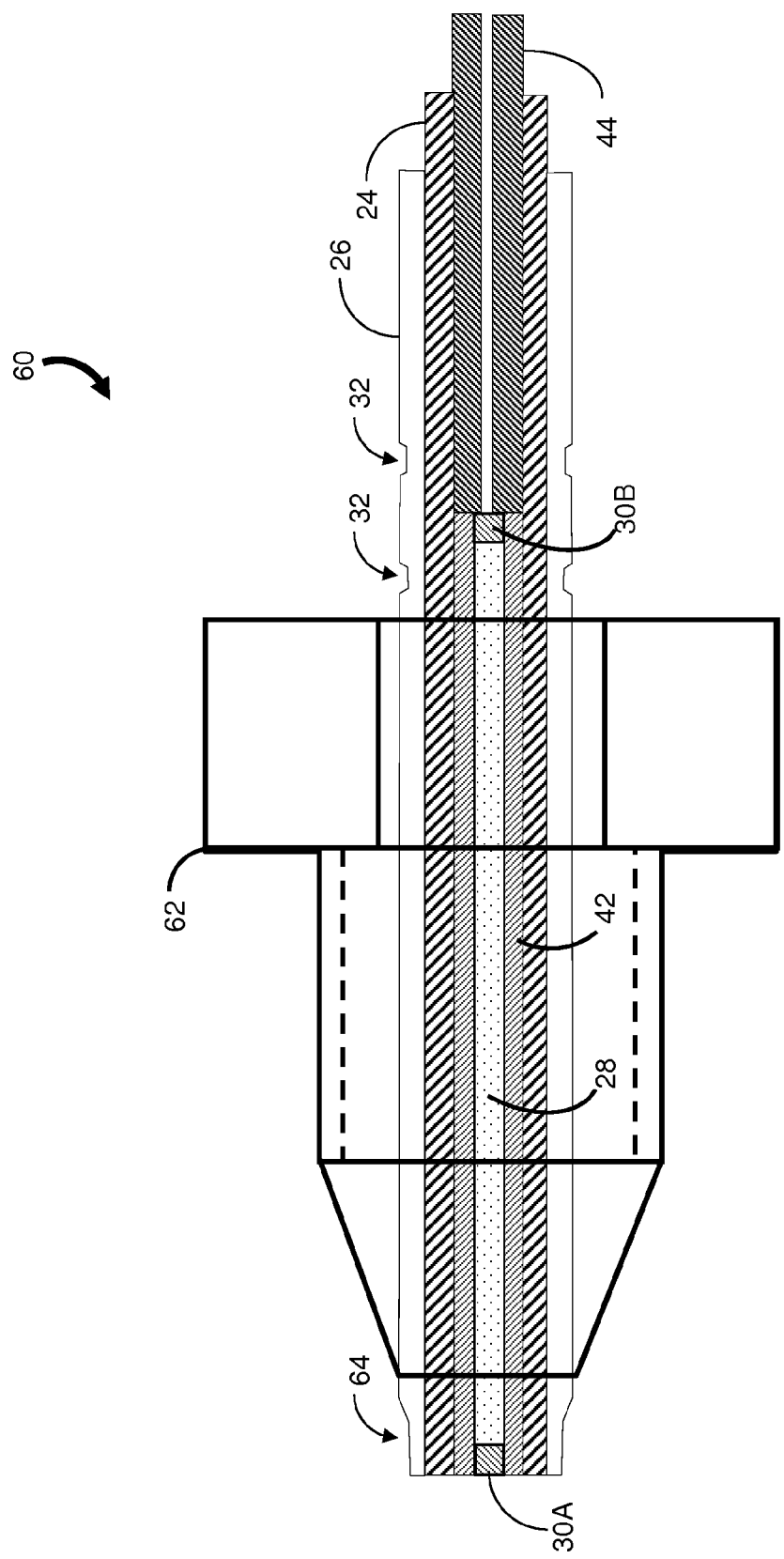
FIG. 6 is a cross-sectional diagram of another embodiment of a chromatography column assembly in accordance with the invention which includes a conventional fitting.

FIG. 6 shows an embodiment of a chromatography column assembly 60 that includes a fitting 62 for fluidic coupling to a port of a fluidic component, such as an inlet port or an outlet port. For example, the fitting 62 may be a conventional compression screw and ferrule assembly. In the illustrated embodiment, the sorbent bed 28, frits 30 and sorbent bed tube 42 are disposed at one end of the assembly 60. The end of the assembly 60 is polished so that the outer tube 26, intermediate tube 24, sorbent bed tube 42 and frit 30A are substantially flush to minimize void volume. A uniform radial crimp 64 is formed at the polished end. In addition, a uniform radial crimp 32 is present on each side of the longitudinal location where the sorbent bed tube 42 abuts the fluid transfer tube 44. The resulting chromatographic assembly 60 is suitable for fluidic couplings at pressures that can exceed 20,000 psi.

Figure 7:
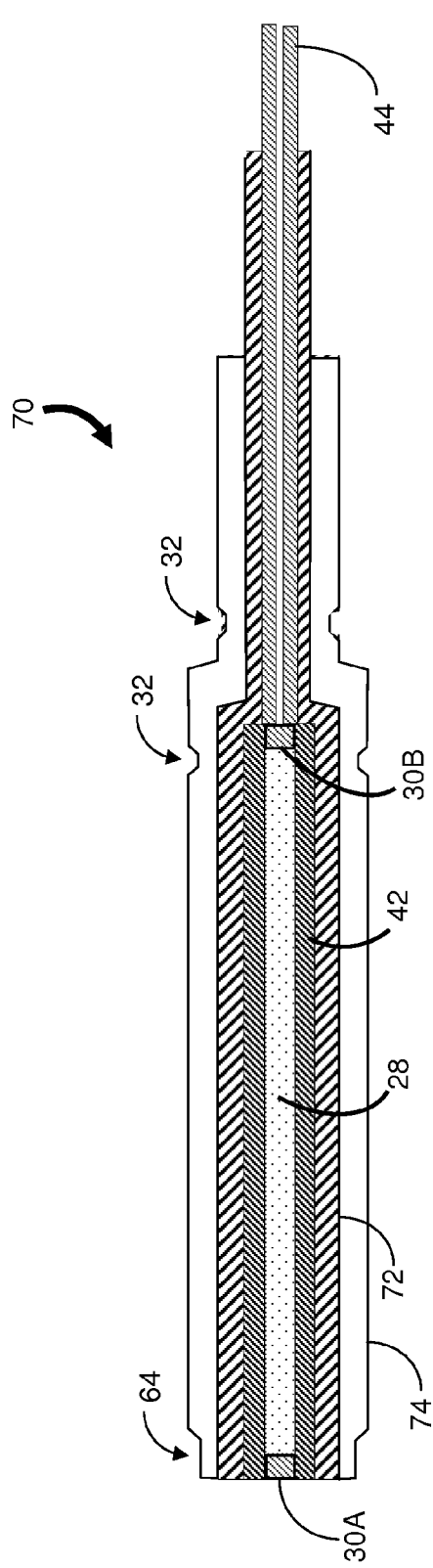
FIG. 7 is a cross-sectional diagram of another embodiment of a chromatography column assembly in accordance with the invention.

FIG. 7 depicts an alternative embodiment of a chromatographic column assembly 70 in which no fitting is present. In addition, the intermediate tube 72 and outer tube 74 have smaller inner and outer diameters in the region of the assembly 70 that surrounds the fluid transfer tube 44. A uniform radial crimp 32 is present on each side of the longitudinal location where the sorbent bed tube 42 abuts the fluid transfer tube 44. The crimped and polished end of the assembly 70 is suitable to interface directly with another fluidic component.

For the chromatographic column assemblies 60, 70 of FIG. 6 and FIG. 7, the inner diameter (ID) and OD of the fluid transfer tube 44 can be same as or different from the ID and OD of the sorbent bed 28, as required for different coupling purposes and flexibility of coupling to external components. In preferred embodiments, the ID of the fluid transfer tube 44 is less than the ID of the sorbent bed 28. By way of specific numerical examples, the ID of the fluid transfer tube 44 can be in a range from 25 µm to 500 µm. The sorbent bed tube 42 of one chromatographic column assembly 60 is shown as having a different ID and the same OD as the fluid transfer tube 44. In contrast, the sorbent bed tube 42 of the other chromatographic column assembly 70 has a different ID and a different OD relative to the fluid transfer tube 44.

In the embodiments shown in FIG. 4 and FIG. 7, one or more of the intermediate tubes 24, 48 and 72 can be fabricated to have two or more different ODs in order to match the ODs of the sorbent bed tube 42 and fluid transfer tube 44. The intermediate and outer tubes 24, 48, 26 and 74 can be manufactured by a variety of techniques, such as laser welding two different tubes together or machining a single tube to have the desired configuration.

Figure 8:
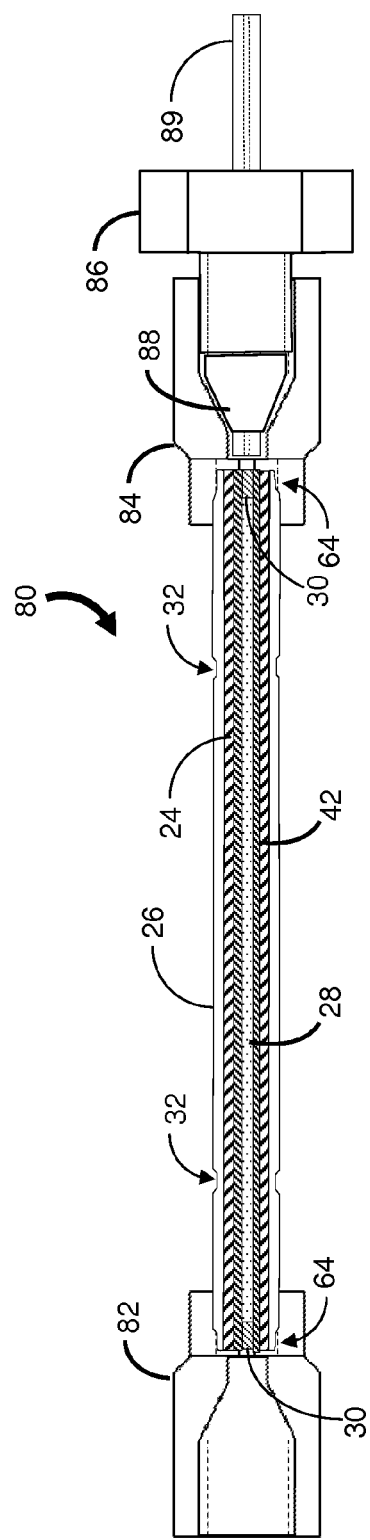
FIG. 8 is a cross-sectional diagram of another embodiment of a chromatography column assembly in accordance with the invention.

An alternative embodiment of a chromatographic column assembly 80 is illustrated in FIG. 8. The sorbent bed 28 is disposed within a sorbent bed tube 42 that extends the full length of the assembly 80. Each end of the assembly 80 is polished so that all tube components are flush at their ends where a uniform radial crimp 64 is formed. Fittings 82 and 84 are used to couple the assembly 80 to other fluidic components, such as chromatography system components. As illustrated, fitting 84 uses a conventional compression type screw 86 and ferrule 88 to couple the assembly 80 to a fluid transfer tube 89. The fluidic couplings can withstand high fluidic pressures, for example, greater than 20,000 psi. In alternative configurations, the fittings may utilize threads, welds and/or glue to achieve the fluidic coupling.

Figure 9:
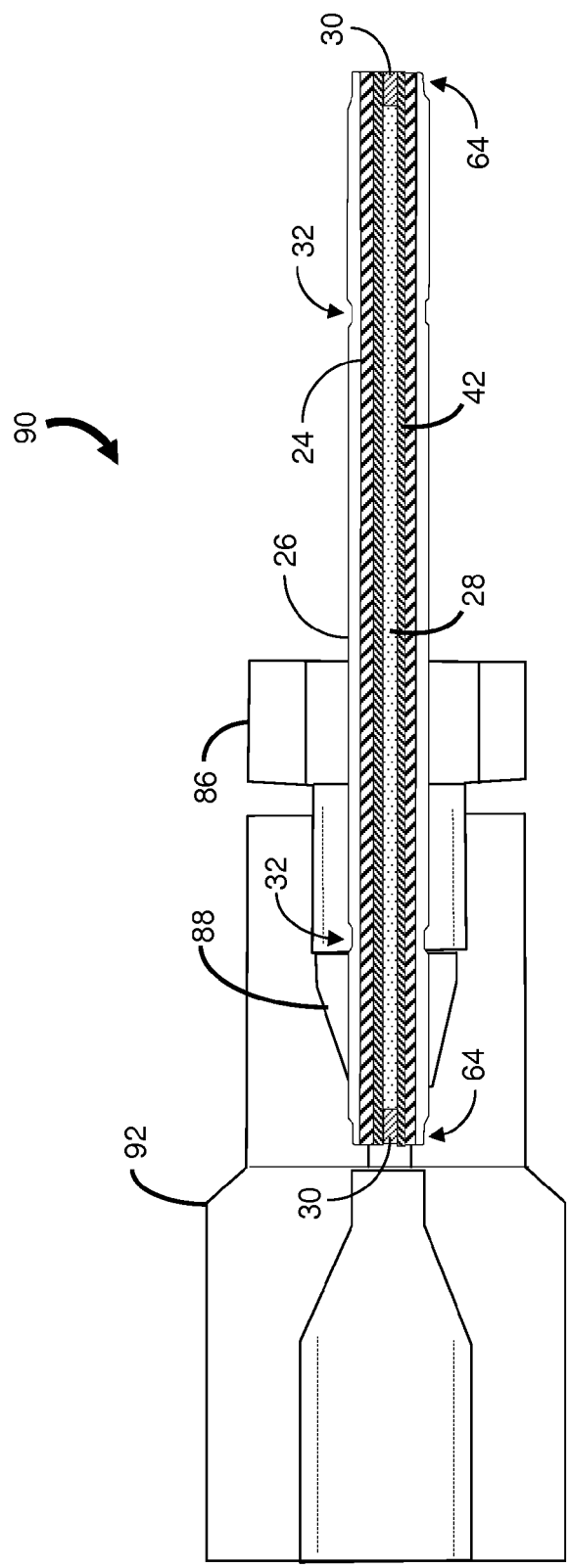
FIG. 9 is a cross-sectional diagram of another embodiment of a chromatography column assembly which includes a conventional fitting.

FIG. 9 shows an alternative embodiment in which a chromatographic column assembly 90 includes a conventional fitting having a compression screw 86, coupling body 92 and ferrule portion 88. The fitting allows the assembly 90 to be coupled to a separate device or system component.

Figure 10A:
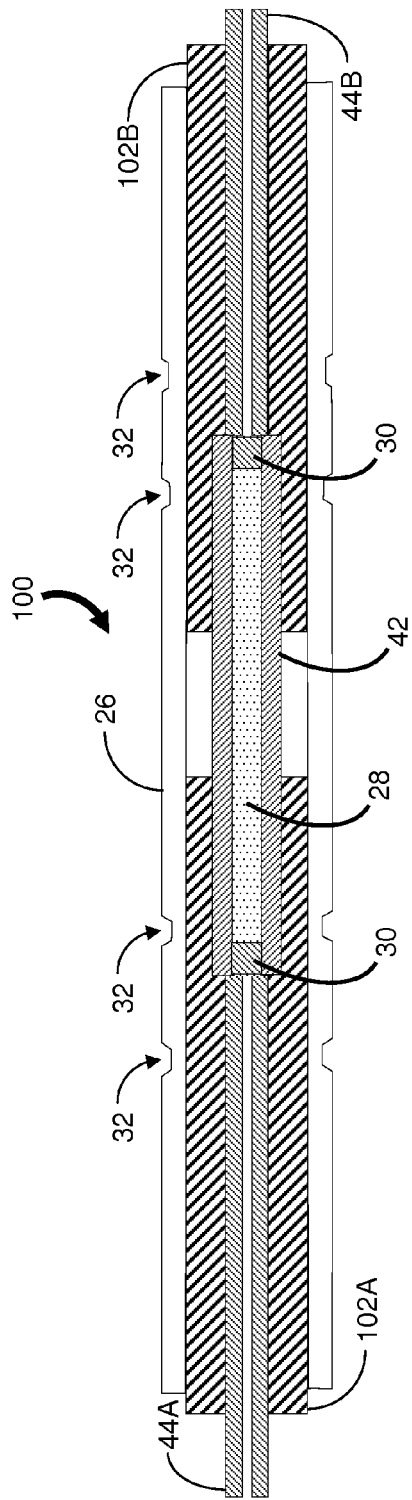
FIG. 10A is a cross-sectional diagram of another embodiment of a chromatography column assembly in accordance with the invention.
Figure 10B:
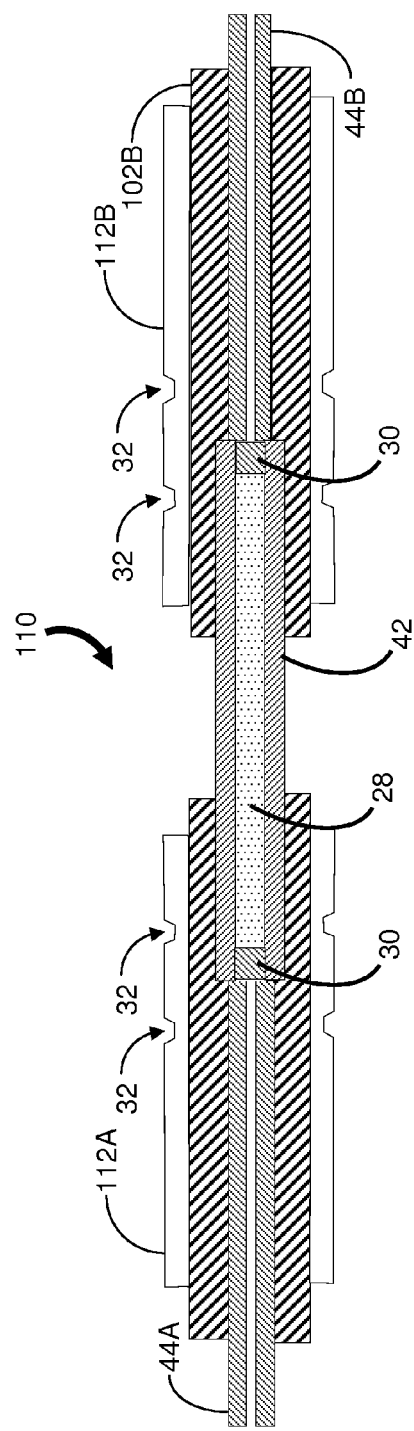
FIG. 10B is a cross-sectional diagram of another embodiment of a chromatography column assembly in accordance with the invention where the outer tube of the assembly of FIG. 10A is provided as two separate pieces.

FIG. 10A shows another embodiment in which a chromatographic column assembly 100 includes two counter-bored intermediate tubes 102A and 102B. A portion of the sorbent bed tube 42 extends into each of the counterbores of the intermediate tubes 102. The internal ends of the two intermediate tubes 102 are separated by a gap while the sorbent bed tube 42 remains protected by the outer tube 26. FIG. 10B shows an alternative embodiment in which a chromatographic column assembly 110 in which the outer tube 26 of FIG. 10A is effectively replaced by two separated outer tubes 112A and 112B. For long or flexible column assemblies, the illustrated embodiment is useful for reducing the stress applied to the sorbent bed tube 42 during the manufacturing process and during operation.

While the invention has been shown and described with reference to specific embodiments, it should be understood by those skilled in the art that various changes in form and detail may be made therein without departing from the spirit and scope of the invention as recited in the accompanying claims.

What is claimed is:

1. A chromatographic column assembly, comprising:
an outer tube comprising a metal;
an intermediate tube comprising a polymeric material and disposed within the outer tube;
a sorbent bed tube disposed within the intermediate tube and having a first end and a second end opposite the first end;
a sorbent bed disposed within the sorbent bed tube;
a first inner tube disposed within the intermediate tube and having a first inner tube end abutting the first end of the sorbent bed tube, thereby defining a first tube interface; and
a second inner tube disposed within the intermediate tube and having a second inner tube end abutting the second end of the sorbent bed tube, thereby defining a second tube interface,
wherein the outer tube is deformed by a first uniform radial crimp at a longitudinal location along the outer tube that spans the first tube interface to form a fluid-tight seal between the first inner tube end and the first end of the sorbent bed tube, wherein the outer tube is deformed by a second uniform radial crimp at a longitudinal location along the outer tube that spans the second tube interface to form a fluid-tight seal between the second inner tube end and the second end of the sorbent bed tube, and wherein the first and second uniform radial crimps each have a substantially flat base region over which a diameter of the outer tube is reduced for a longitudinal length, wherein the longitudinal length of the substantially flat base regions of the first and second uniform radial crimps are each at least one millimeter.

2. The chromatographic column assembly of claim 1 further comprising a pair of frits, one of the frits disposed at an end of the sorbent bed and the other of the frits disposed at an opposite end of the sorbent bed.

3. The chromatographic column assembly of claim 2 wherein each of the frits is disposed within the sorbent bed tube and at an end of the first inner tube.

4. The chromatographic column assembly of claim 2 wherein one of the frits is disposed within the first inner tube at the first inner tube end and the other of the frits is disposed within the second inner tube at the second inner tube end.

5. The chromatographic column assembly of claim 1 wherein an inner diameter of the sorbent bed tube is different from an inner diameter of at least one of the first inner tube and the second inner tube.

6. The chromatographic column assembly of claim 1 wherein an outer diameter of the sorbent bed tube is different from an outer diameter of at least one of the first inner tube and the second inner tube.

7. The chromatographic column assembly of claim 1 wherein the sorbent bed tube comprises fused silica.

8. The chromatographic column assembly of claim 7 wherein the sorbent bed tube and the intermediate tube are formed as an integrated structure.

9. The chromatographic column assembly of claim 1 wherein the sorbent bed tube comprises stainless steel.

10. The chromatographic column assembly of claim 9 wherein the sorbent bed tube and the intermediate tube are formed as an integrated structure.

11. The chromatographic column assembly of claim 1 wherein the intermediate tube has a length that is the same as a length of the sorbent bed tube and further comprising a pair of additional intermediate tubes each disposed within the outer tube and having an end abutting an end of the intermediate tube.

12. The chromatographic column assembly of claim 1 further comprising a ferrule disposed on the outer tube proximate to one end of the outer tube for engaging a coupling body at a fluid port.

13. The chromatographic column assembly of claim 1, wherein the first and second uniform radial crimps each have a transition region on each side of the substantially flat base region that transitions between the reduced diameter of the substantially flat base region and an uncrimped outer diameter of the outer tube.

14. The chromatographic column assembly of claim 1, wherein the first and second uniform radial crimps are each formed by a collet having a machined circular bore.

15. A chromatographic column assembly, comprising:
an outer tube comprising a metal;
an intermediate tube comprising a polymeric material and disposed within the outer tube;
a sorbent bed tube formed of fused silica and disposed within the intermediate tube, the sorbent bed tube having a first end and a second end;
a sorbent bed disposed within the sorbent bed tube;
a first inner tube disposed within the intermediate tube and having a first inner tube end abutting the first end of the sorbent bed tube, thereby defining a first tube interface;
a second inner tube disposed within the intermediate tube and having a second inner tube end abutting the second end of the sorbent bed tube, thereby defining a second tube interface; and
a pair of frits, each of the frits disposed at an end of the sorbent bed,
the outer tube being deformed by a first uniform radial crimp at a longitudinal location that spans the first tube interface to thereby form a fluid-tight seal between the outer tube, intermediate tube, sorbent bed tube and one of the frits, and the outer tube being deformed by a second uniform radial crimp at a longitudinal location that spans the second tube interface to thereby form a fluid-tight seal between the outer tube, intermediate tube, sorbent bed tube and the other of the frits, the first and second uniform radial crimps each having a substantially flat base region over which a diameter of the outer tube is reduced for a longitudinal length, wherein the longitudinal length of the substantially flat base regions of the first and second uniform radial crimps are each at least one millimeter.

16. The chromatographic column assembly of claim 15 wherein the outer tube has two ends and further comprising a first fitting disposed on the outer tube at one of the ends and a second fitting disposed on the outer tube at the other one of the ends.

17. The chromatographic column assembly of claim 15 wherein an inner diameter of the sorbent bed tube is different from an inner diameter of at least one of the first and second inner tubes.

18. The chromatographic column assembly of claim 15 wherein an outer diameter of the sorbent bed tube is different from an outer diameter of at least one of the first and second inner tubes.

19. The chromatographic column assembly of claim 15, wherein the first and second uniform radial crimps each have a transition region on each side of the substantially flat base region that transitions between the reduced diameter of the substantially flat base region and an uncrimped outer diameter of the outer tube.

20. The chromatographic column assembly of claim 15, wherein the first and second uniform radial crimps are each formed by a collet having a machined circular bore.

* * * * *